United States Patent [19]

McDonald

[11] Patent Number: 5,662,659

[45] Date of Patent: *Sep. 2, 1997

[54] ENDWISE ADJUSTABLE EYE FORCEPS

[76] Inventor: Henry H. McDonald, 319 Arlington Dr., Pasadena, Calif. 91105

[*] Notice: The term of this patent shall not extend beyond the expiration date of Pat. No. 5,292,324.

[21] Appl. No.: 560,348

[22] Filed: Nov. 17, 1995

Related U.S. Application Data

[63] Continuation of Ser. No. 155,598, Nov. 22, 1993, abandoned, which is a continuation-in-part of Ser. No. 33,377, Mar. 18, 1993, Pat. No. 5,292,324.

[51] Int. Cl.⁶ ........................................ A61F 9/00
[52] U.S. Cl. ................................ 606/107; 606/205
[58] Field of Search ..................... 606/205–211, 107, 606/167, 171; 623/4, 6

[56] References Cited

U.S. PATENT DOCUMENTS

| | | |
|---|---|---|
| 1,837,277 | 12/1931 | Lund . |
| 3,980,086 | 9/1976 | Kletschka et al. . |
| 4,257,406 | 3/1981 | Schenk . |
| 4,573,998 | 3/1986 | Mazzocco . |
| 4,785,816 | 11/1988 | Baccala et al. . |
| 4,813,957 | 3/1989 | McDonald . |
| 4,844,065 | 7/1989 | Faulkner . |
| 4,959,070 | 9/1990 | McDonald . |
| 5,007,913 | 4/1991 | Dulebohn et al. ................ 606/107 |
| 5,100,410 | 3/1992 | Dulebohn . |
| 5,135,530 | 8/1992 | Lehmer . |
| 5,147,368 | 9/1992 | Brown . |
| 5,178,622 | 1/1993 | Lehner, II . |
| 5,217,464 | 6/1993 | McDonald . |
| 5,222,960 | 6/1993 | Poley . |
| 5,292,324 | 3/1994 | McDonald ........................ 606/205 |

FOREIGN PATENT DOCUMENTS

| | | |
|---|---|---|
| 2555952 | 7/1985 | France . |
| 361627 | 5/1921 | Germany . |
| 119055 | 9/1918 | United Kingdom . |

Primary Examiner—Glenn Dawson
Attorney, Agent, or Firm—William W. Haefliger

[57] ABSTRACT

An improved intraocular lens forceps, including a first and second arm, the first arm has a first handle and a first lens engagement blade spaced from the first handle. The second arm has a second handle and a second lens engagement blade spaced from the second handle. The blades extend generally longitudinally in laterally spaced relation and at opposite side of a bisecting plane. The first arm has a primary section and a secondary section. The secondary arm sections extend between the first handle and first blade. The second arm has a primary section and a secondary section, the secondary arm sections extend between the second handle and second blade. The blades are movable by the handles and arm sections between closed and open positions relative to the lens. The alarm primary sections extend in cross-over relation to define a cross-over locus, when the blades are in closed position; and the secondary arm sections extend generally longitudinally in substantially parallel and elongated relation, and with spacing therebetween less than about 3 mm.

26 Claims, 10 Drawing Sheets

ENDWISE ADJUSTABLE EYE FORCEPS

This application is a continuation of application Ser. No. 08/7155,598, filed Nov. 22, 1993, now abandoned, which is a continuation-in-part of Ser. No. 08/033,377, filed Mar. 18, 1993, continuation in part of U.S. patent application Ser. No. 08/033,377, filed Mar. 18, 1993, now U.S. Pat. No. 5,292,329.

BACKGROUND OF THE INVENTION

This invention relates generally to intraocular lens implantation, and more particularly concerns apparatus and method for achieving such implantation via a very small surgical incision in the corneo-scleral limbus of the eye.

In the past, forceps have been used with blades that clamp the plastic lens for introducing it into the eye via a relatively wide wound or incision in the corneo-scleral limbus. A typical wound was required to have a width of about 7–15 millimeters in order to pass the forcep blades and to allow spreading of the blades to release the plastic lens in the eye.

Problems encountered included laceration of the elastic silicon lens, and undesirable sudden release and rapid unfolding of the lens (as opposed to gentle release) causing injury to intraocular tissue, due to inability to separate the blades widely and gently. The usual wide incision is undesirable due to the amount of suturing required to close the wound, and time required for such suturing, increased or undesirably long convalescence time, increase in astigmatic complications, difficulty in preventing collapse of the intraocular chambers during the operation, and increased risk of post-operative complications. Further, plastic lenses could and did at times become captured by the blades of prior forceps, requiring dangerous instrumentation to release the lens from the grasp of such forceps. The invention of U.S. Pat. No. 4,513,957 represents one approach to the solution of this problem.

Additionally, one of the most significant advances in the surgical procedure of phoco-emulsification which has now become foremost for high volume eye surgeons is that of cracking the extra hard brittle central nuclear lens mass into smaller more readily manageable pieces. This has been particularly difficult, and has forced fine surgeons to abandon phoco-emulsification as their standard procedure for the extraction of a cataract.

Also, there is need for an instrument capable of dilating the eye pupil, as during a cataract operation.

SUMMARY OF THE INVENTION

It is a major object of the invention to provide improved method and apparatus, overcoming the above problems and difficulties. Basically the invention permits wide separation of the blades, adjusted blade positioning in the eye, controlled release of the folded lens within the eye, while motion is transmitted to the blades via a very narrow incision; and controlled cracking of the nuclear lens mass.

The apparatus is usable for implanting a plastic lens into the eye lens zone from which a natural but cataractous lens has just been removed (or removed in the past) as via a narrow surgical incision in the corneo-scleral limbus, and while using a forceps having blades projecting from or beyond arm portions typically defining a cross-over locus in blade open positions, the apparatus movable endwise in the narrow slit to enable precise positioning of the lens prior to its release by the blades. Such apparatus comprises a) first and second arms, the first arm having a first handle and a first lens engagement blade spaced from the first handle, the second arm having a second handle and a second lens engagement blade spaced from the second handle, the blades extending generally longitudinally in laterally spaced relation and at opposite side of a bisecting plane, b) the first arm having primary and secondary arm sections extending between the first handle and first blade, the second arm having primary and secondary arm sections extending between the second handle and second blade, the blades being movable by the handles and arm sections between closed and open positions relative to the lens, the arm primary sections extending in cross-over relation to define a cross-over locus, when the blades are in closed position, and c) the secondary arm sections extending generally longitudinally in substantially parallel relation and positioned such that when the blades are in their closed positions one secondary arm section extends at one side of the plane bisecting the forceps, and the other secondary arm section extends at the other side of that plane, and when the blades are the open positions the one secondary arm section extends at the other side of the plane and the other secondary arm section extends at the one side of the plane.

Typically, the secondary arm sections have lengths greater than their maximum lateral separation, to allow movement thereof back and forth in an incision or wound in the eye corneo-scleral limbus via which the blades and lens are inserted into the eye.

Another object includes providing a first blade as referred to which remains at said one side of the bisecting plane as the blades are moved between said closed and open positions, and the second blade remains at said other side of said plane as the blades are moved between said closed and open positions. Also, the first handle typically remains at said other side of said plane as the blades are moved between said closed and open positions, and the second handle remains at said one side of said plane as the blades are moved between said closed and open positions.

Yet another object is to provide secondary arm sections which have substantially equal lateral separation in said closed and open positions of the blades. In this regard, the primary arm sections are everywhere laterally separated when the blades are in closed position; also the primary arm sections extend at opposite angles relative to said plane, and they have lengths substantially less than the longitudinal lengths of said secondary arm sections.

A further object is to provide blades which have lens gripping tongs projecting toward said plane, to grip opposite sections of the folded lens, the tongs defining pivots about which the folded lens may pivot during unfolding release of the lens as the blades are moved from closed to open positions. In this regard, the tongs are typically located at tips of the blades remote from the arm cross-over locus. For example, the tongs may be attached to end portions of the blades, or may be located or attached closer to the root ends of the blades, to allow preferential expansion and escape of the lens implant in a manner desired by the surgeon, and as will be seen. The gripped lens is folded, and the tongs pushed into local portions of the folded blades to enable pivoting of the lens as it is controllably released by blade separation, with the tongs continuing to controllably locate the lens as it unfolds or expands.

The improved forceps is not only useful as an intraocular lens holder, but also as a utility forceps, capable of passing through a small puncture wound to insert a lens implant, or grasp an intraocular foreign body or a tissue for its removal or better positioning—all through the small puncture wound. The forceps is therefore usable for other purposes where maximum maneuvering within a small slit or wound is desired, for example.

Another object is to provide an improved intraocular lens forceps, comprising a) first and second arms, the first arm having a first handle and a first lens engagement blade spaced from the first handle, the second arm having a second handle and a second lens engagement blade spaced from the second handle, the blades extending generally longitudinally in laterally spaced relation and at opposite side of a bisecting plane, b) the first arm having a primary section and a secondary section, the secondary arm sections extending between the first handle and first blade, the second arm having a primary section and a secondary section, the secondary arm sections extending between the second handle and second blade, the blades being movable by the handles and arm sections between closed and open positions relative to the lens, the arm primary sections extending in cross-over relation to define a cross-over locus, when the blades are in said closed position, c) the secondary arm sections extending generally longitudinally in substantially parallel relation at opposite sides of said plane, and with spacing therebetween less than about 4 mm.

Typically, when the blades are increasingly separated from one another, the spacing between the secondary arm sections is decreased.

Further, the blades may have jaw edges to engage and separate opposite sides of a groove formed in an eye lens hardened nucleus when the blades are increasingly separated, thereby to fracture the hardened nucleus. Such edges may diverge from one another in the direction of the plane.

Another object is to provide blades which, when in closed position have combined thickness less than about 3 mm. The blades may have notches therein openly facing away from the plane, for gripping and separating edges of an eye pupil when the blades are moved apart.

In accordance with a further object, the secondary arm sections are positioned such that when the blades are in closed positions one secondary arm section extends at one side of the plane and the other secondary arm section extends at the other side of the plane, and when the blades are in open positions one secondary arm section extends at the other side of the plane and the other secondary arm section extends at one side of the plane.

Finally, the secondary arm sections may have maximum lateral separation, and longitudinal lengths greater than their maximum lateral separation to allow movement back and forth in an incision would in the eye corneo-scleral limbus via which the blades and lens are inserted into the eye.

These and other objects and advantages of the invention, as well as the details of an illustrative embodiment, will be more fully understood from the following specification and drawings, in which:

DRAWING DESCRIPTION

FIG. 33 is a perspective view of the FIG. 32 instrument;

FIG. 34 is a section taken on lines 34—34 of FIG. 32;

FIG. 34a is a section taken on lines 34a—34a of FIG. 32a; and

FIG. 35 is an enlarged section, like 34 showing blade location in an eye pupil to be dilated;

FIG. 36 shows a modified forceps.

DETAILED DESCRIPTION

Figure 1:
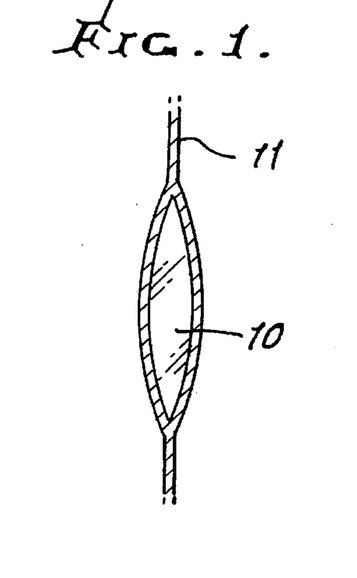
FIG. 1 is a side view of a cataractous opaque lens.
Figure 2:
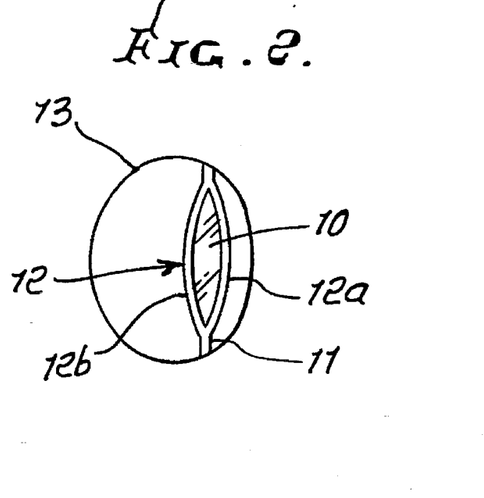
FIG. 2 is a side view of the cataractous opaque lens within the lens capsule in the eye.
Figure 3:
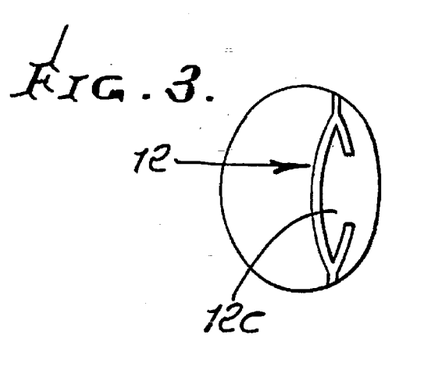
FIG. 3 is a side view of the anterior lens capsule after removal of the opaque cataract lens and the central portion of the anterior capsule.
Figure 4:
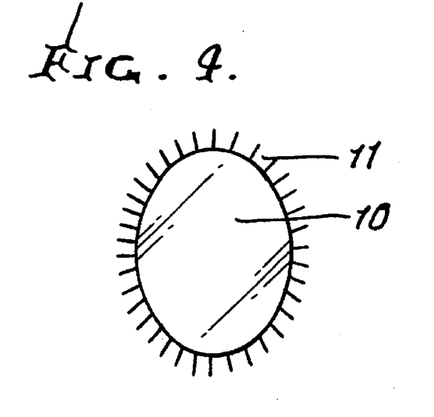
FIG. 4 is a front view of the cataractous lens as seen in FIG. 1, showing zonula fibers holding the capsule.
Figure 17:
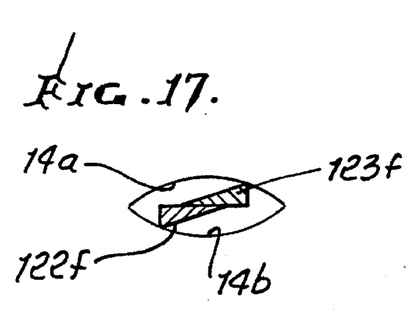
FIGS. 17, 19 and 21 are end views of the instrument arms in FIGS. 16, 18 and 20, respectively.

Referring first to FIGS. 1 and 2, they show in side view, and schematically, a cataractous opaque lens 10, bounded peripherally by zonula fibers 11, and located between anterior and posterior portions 12a and 12b of the lens capsula. The eye outline appears schematically at 13, and FIG. 17 is a section accurately showing corresponding parts, as well as other parts, of the eye. FIG. 3 shows the capsule void 12c after removal of the cataractous lens tissue. FIG. 4 is a front view of the lens 10 seen in side view in FIG. 1.

Figure 5:
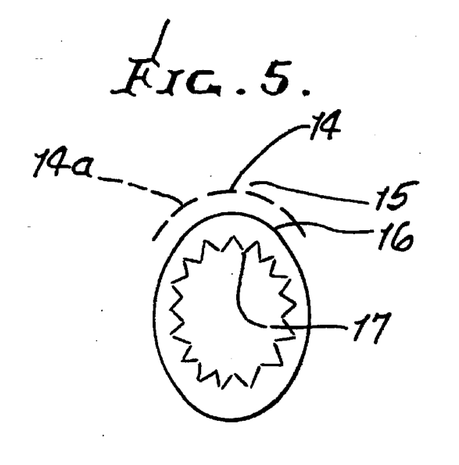
FIG. 5 is a front view showing the location of a surgical 1 to 3 mm incision in the coroscleral tissue, outwardly from the limbus.

FIG. 5 is a schematic frontal view of the eye, showing a narrow (for example about 3 mm wide) incision or puncture 14 in the corneoscleral tissue 15, at a short distance (as for example about 2 mm) from the limbus 16, the latter designating the merging of light (sclera) and dark (iris periphery) zones of the eye. The present invention makes possible the use of such a narrow, i.e. short, puncture wound, as opposed to the prior very wide incision, indicated by broken lines 14a, which was necessary in order to implant a plastic or silicon lens into the capsula 12. Such a wide (typically 15–18 mm) incision requires much more suturing than is required for the short incision or puncture wound 14, and requires a longer convalescence period, with increased risk of post-operative complications. The cataractous lens is more recently removed by phacoemulsification with ultrasonic vibration fragmentation and aspiration via the puncture 14, leaving jagged anterior "leaves" or serrations 17 in the anterior capsula portion 12a; the posterior capsula portion 12b remains clear. Anterior capsulatomy removes the central anterior capsula, leaving space indicated at 12c in FIG. 3.

Figure 6:
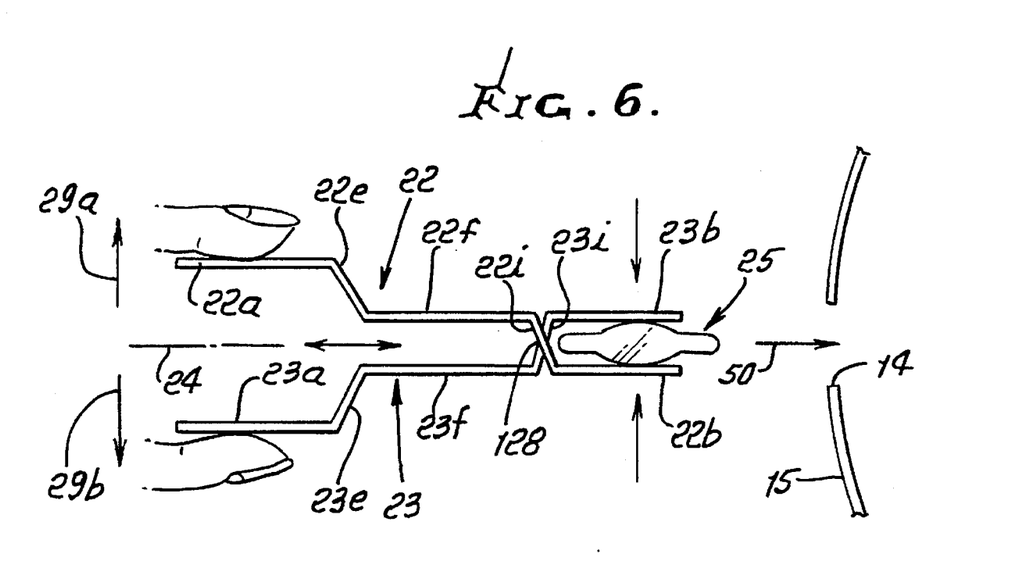
FIG. 6 is a view showing the forceps of the invention in folded lens gripping position.
Figure 7:
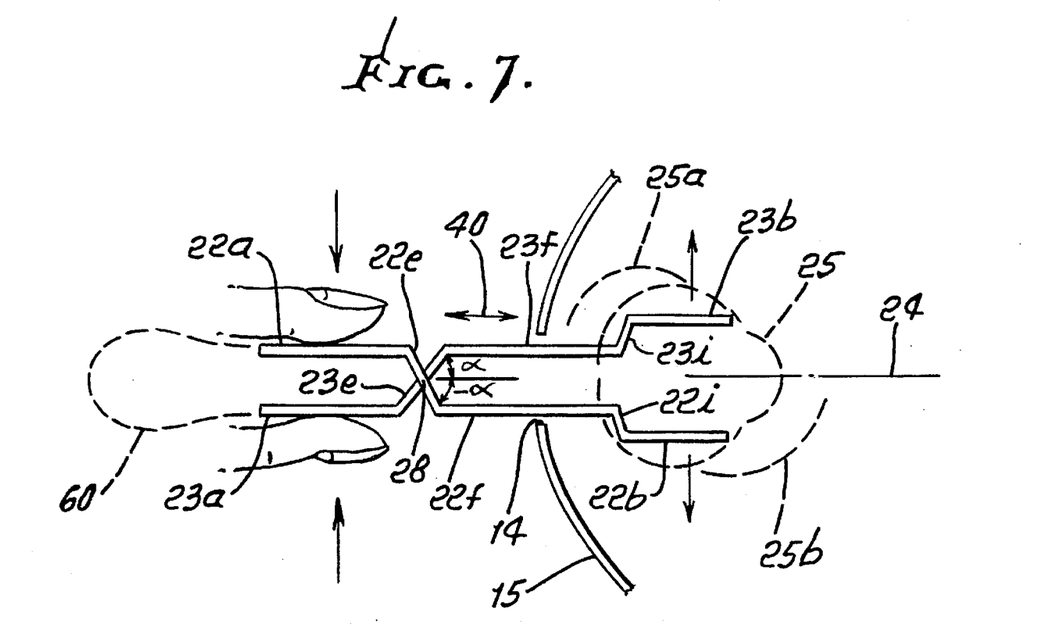
FIG. 7 is a view like FIG. 6, but showing the forceps in lens release position.
Figure 12:
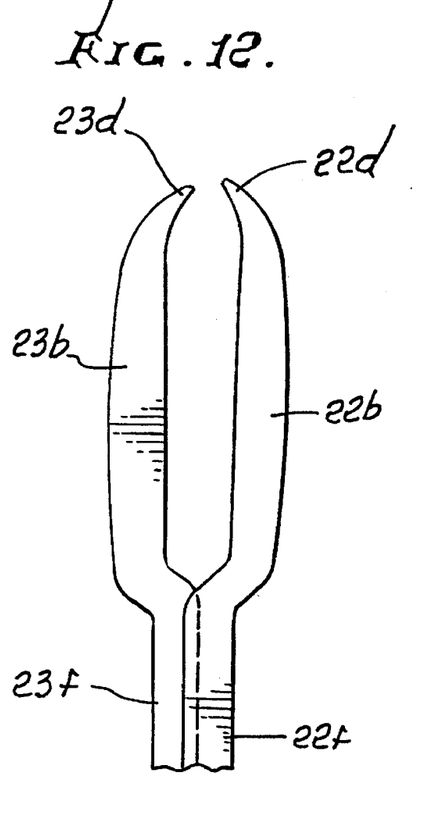
FIGS. 12 and 13 are side and end views of arm sections that extend in a convex-convex sided wound during lens insertion into the eye.

Referring to FIGS. 6 and 7, the forceps of the present invention include first and second arms 22 and 23, the first arm having a first handle 22a and a first lens engagement blade 22b spaced endwise forwardly from handle 22a. The second arm 23 is a mirror image of arm 22, relative to a longitudinally forwardly extending central plane 24 bisecting the forceps. Second arm 23 has a second handle 23a and a second lens engaging blade 23b spaced endwise forwardly of handle 23a. Handles 22a and 23a are laterally spaced apart, and movable from lens grip positions as during lens insertion through slit 14 (puncture wound) in corneoscleral tissue 15; i.e. from position as shown in FIG. 6 to position as shown in FIG. 7. At the same time, the blades are relatively movable laterally from FIG. 6 to FIG. 7 position, i.e. from position gripping folded plastic or silicon lens 25 to position releasing that lens (in FIG. 7) for controlled unfolding and implantation in selected position (in longitudinal direction 50) in the eye, without widening the narrow slit. Note that blades 22b and 23b extend generally longitudinally in laterally spaced relation relative to and at opposite sides of central plane 24 that bisects the forceps. As will be seen, the blades may taper forwardly as seen in FIG. 12, and may have blunt opposed tongs 22d and 23d at the blade tips, that slightly push into the folded lens to provide pivot points for lens pivoting to enable controlled release and expansion of the lens while it remains positioned endwise relative to the blades, for precision positioning in the eye.

The arm 22 also has primary and secondary arm sections 22e and 22f extending between the handle 22a and blade 22b; and the second arm likewise has primary and secondary arm sections 23e and 23f extending between handle 23a and blade 23f. Sections 22e and 23e extend in cross-over relation, as at 28, to define a cross-over locus when the blades are in open position; however, when the blades are moved together to grip the folded lens, i.e. as by allowing the handles to spring apart in directions 29a and 29b, the cross-over locus 28 disappears, whereas a cross-over locus is formed at 128 spaced rightwardly of sections 22e and 23e. See FIG. 6. Note that, in general, the blades are movable by finger pressure on the handles 22a and 23a, as shown, to move the blades between open and closed positions, relative to the lens. In FIG. 7, the lens is shown as rotating and expanding from folded position toward unfolded position. Lens haptics appear at 25a and 25b. The handles are typically connected by a resiliently deflectable metal spring loop, indicated at 60.

In accordance with an important aspect of the invention, the secondary arm sections 22f and 23f extend generally longitudinally in substantially parallel relation and positioned such that when the blades are in said closed positions one secondary arm section extends at one side of plane 24 and the other secondary arm section extends at the other side of said plane, and when the blades are in said open positions said one secondary arm section extends at said other side of said plane and said other secondary arm section extends at said one side of said plane. Typically, the secondary arm sections 22f and 23f have longitudinal length greater than their maximum lateral separation to allow movement thereof back and forth in an incision wound in the eye corneo-scleral limbus via which the blades and lens are inserted into the eye.

During handle movement to move arm sections 22f and 23f between FIG. 6 and 7 positions, the first blade 22b remains at the one side of the plane as the blades are moved between the closed and open positions, and the second blade remains at the other side of the plane as the blades are moved between the closed and open positions. In addition, the first handle 22a remains at the other side of the plane as the blades are moved between the closed and open positions, and the second handle 23a remains at the one side of the plane as the blades are moved between the closed and open positions.

It should be noted that the arms, handles and blades remain in FIG. 6 position during lens insertion into the eye, and while the lens is accurately positioned, longitudinally, in direction 50, as enabled by longitudinal elongation of arm sections 22f and 23f, which sections can move back and forth in the wound or slit without widening their separation, even during eventual lens release while the blades are held against further longitudinal movement. In this regard, note that in FIGS. 6 and 7, the arm secondary sections 22f and 23f have substantially equal lateral separation in the closed and open positions of the blades and they move closer together during blade movement between FIG. 6 and FIG. 7 position. Thus, the slit or wound can be kept minimized, and the arm sections 22f and 23f can be moved back and forth, and rotated, in the wound, to enable very accurate lens and haptics positioning. As previously stated, and as shown in FIG. 7, the arm primary sections 22e and 23e are everywhere laterally separated when the blades are in closed position. Note that sections 22e and 23e in FIG. 7 extend at opposite angles α and −α, relative to plane 24; also, sections 22e and 23e have lengths substantially less than the longitudinal lengths of arm sections 22f and 23f.

In FIG. 6 the arm cross-over (cross-fixation) point or locus 128 defined by arm sections 22i and 23i is very close to the blades, whereby the blades are held near one another, with the folded lens therebetween, for insertion through the narrow puncture. Once insertion is completed, and the blades adjusted longitudinally to position the lens, the blades are allowed to slowly separate as by slow increase of manual pressure on the handles 22a and 23a of the forceps. This allows ultimate wide separation of the blades, to between 4 to 6 mm, as seen in FIG. 7 without restriction imposition by the small narrow slit or puncture. The width of the puncture is less than about 3 mm. The blades remain approximately parallel during their excursions.

Note that two different longitudinally spaced cross-over loci, at 24 and 128 are provided, one being operative as in FIG. 6, and the other as in FIG. 7.

Figures 8, 9:
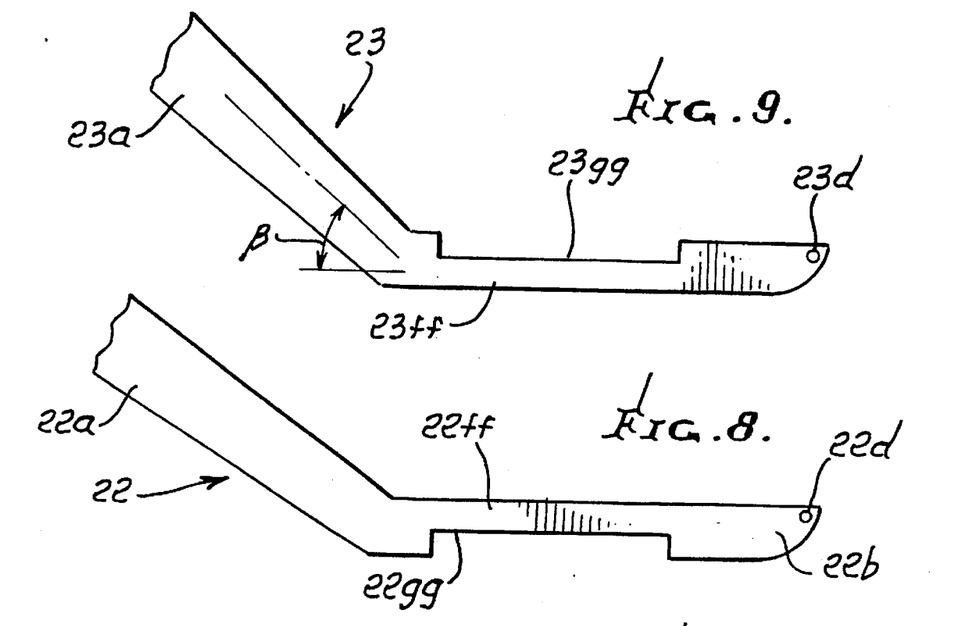
FIGS. 8 and 9 are side elevations showing cut-outs in elongated sections of the forceps arms.
Figure 9A:
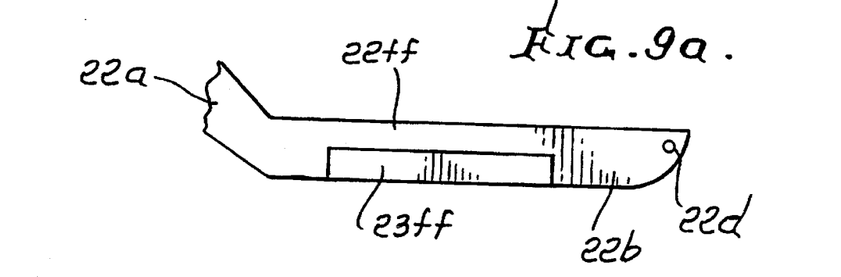
FIG. 9a shows the FIG. 8 and 9 arms in assembled relation.
Figure 10:
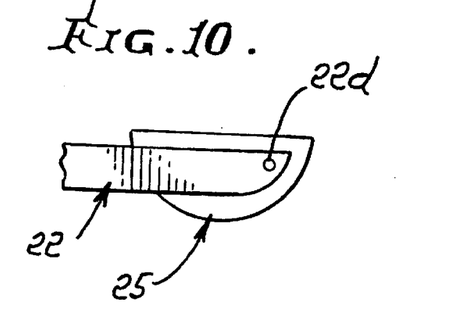
FIGS. 10 and 11 are side elevations showing progressive tilting or extraction of a lens during its release by separating blades.
Figure 11:
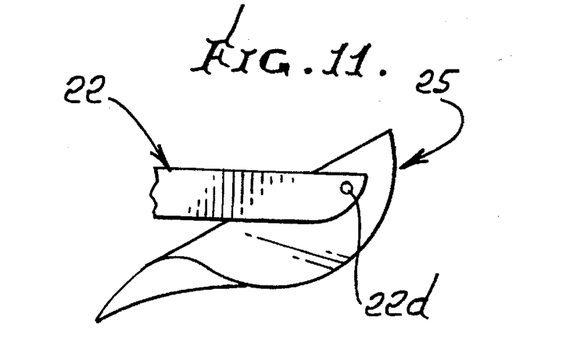

FIG. 8 shows an arm 22 in side elevation, with elements labeled as in FIGS. 6 and 7. Note the cut-out 22gg in arm section 22ff, at the bottom thereof. FIG. 9 is like FIG. 8, but the cut-out 23gg in section 23ff is at the top of that section, of arm 23. The arm handles 22a and 23a extend at an upward angle β, relative to the length directions of 22ff and 23ff. Each blade has a blunt tang or tong at its tip to press into the opposite sides of the folded lens, and act as a lens pivot during lens release, as the blades are separated to FIG. 7 position. See tongs 22d and 23d, as in FIG. 12. FIG. 9a shows the FIG. 8 and 9 arms and blades in side-by-side position, as in use, whereas FIGS. 8 and 9 show them separated for illustration. FIGS. 10 and 11 show such progressive folded lens 25 pivoting, about the axis defined by the two lens engaging opposed tangs or tongs, as the blades separate, allowing controlled release, unfolding and positioning of the lens. In FIG. 11, the lens rotates slowly counterclockwise, under control, during release. If the pivots or tongs are not at the blade tips, but near the blade ends as in FIG. 18a, see 22d' and 23d', the lens rotates clockwise during release.

Figure 13:
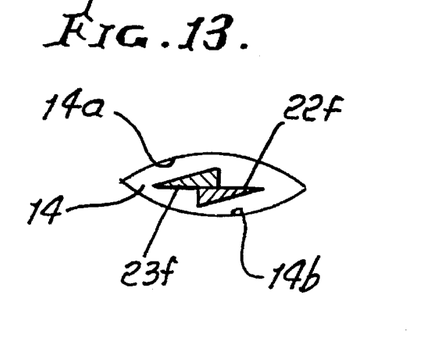
Figure 14:
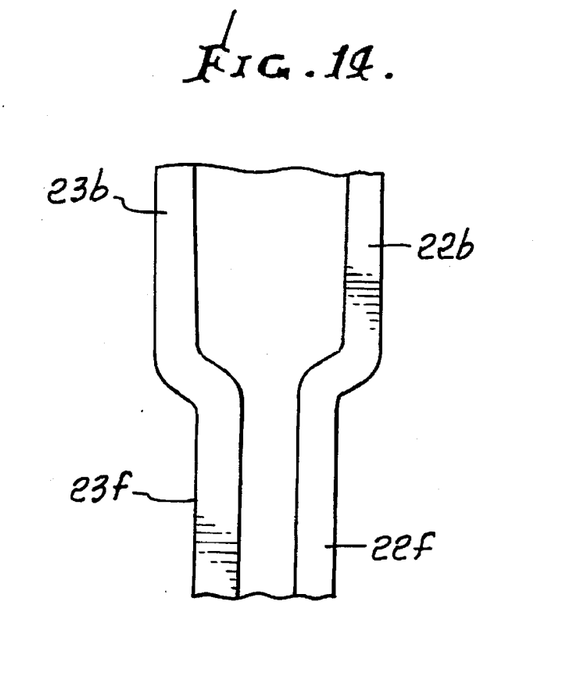
FIGS. 14 and 15 are side and end views of arm sections that extend in a convex-convex sided wound, as during lens release in the eye.
Figure 15:
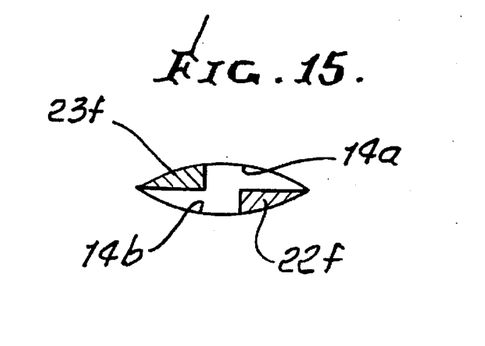

FIGS. 12 and 13 show the positions of the wedge shaped cross-section arm sections 22f and 23f, between concave walls 14a and 14b of a slit 14, as the sections begin to move from FIG. 6 position toward FIG. 7 position. FIGS. 14 and 15 show the positioning of the sections 22f and 23f between concave walls 14a and 14b, in FIG. 7 positions of the arms, the wedge shaped arm sections fitting the seat wall shapes in FIG. 15.

Figure 16:
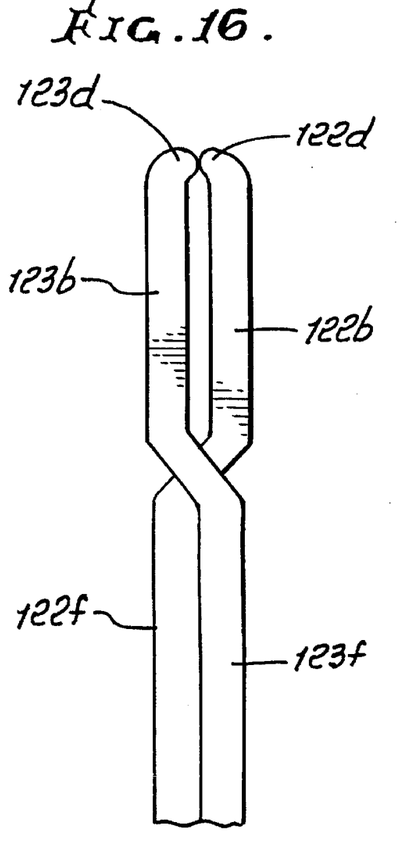
FIGS. 16, 18 and 20 are views of an instrument during progressive lens release.
Figure 18:
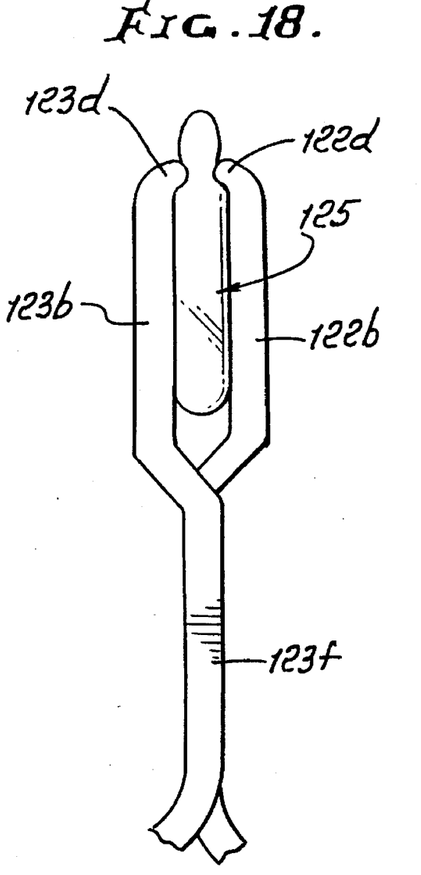
Figures 18A, 20:
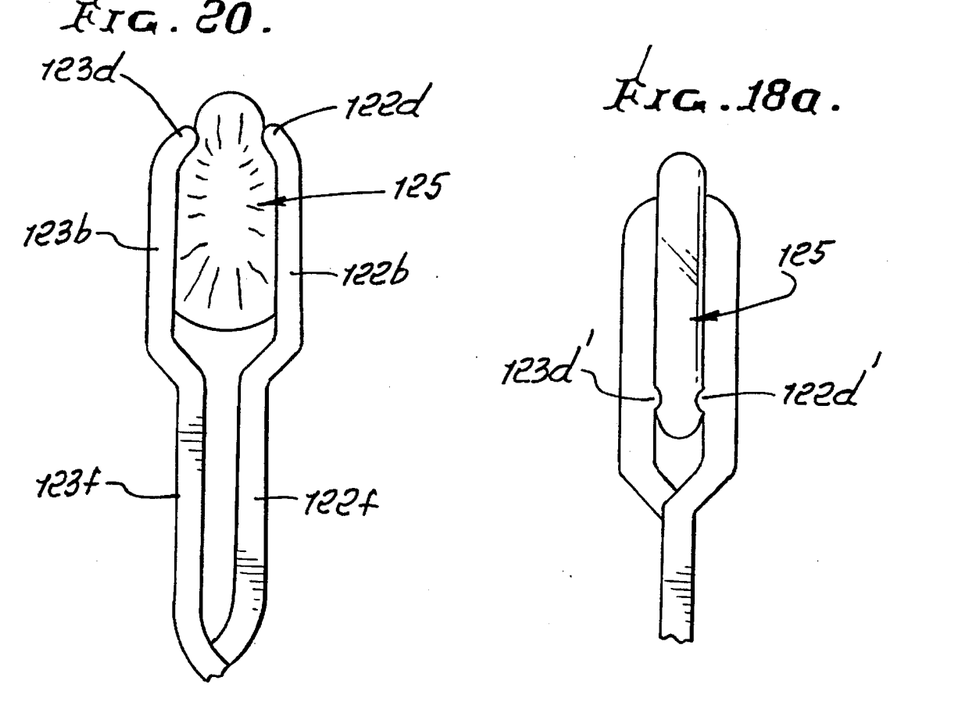
FIGS. 18a is a modified form of FIG. 18.
Figure 19:
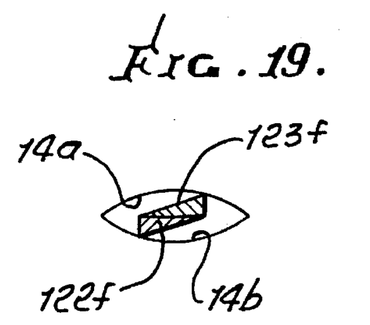

FIG. 16 is another view of blades and arms, 122f, 123f, 122b and 123b, corresponding to these elements seen in FIG. 6. Note that in FIG. 16 the blades are closed toward one another so that tongs 122d and 123d touch. The arms, in wedge shaped cross-section appear in FIG. 17, relative to slit or puncture walls, arm 122f being to the right of arm 123f. In FIG. 18 the arms now appear superimposed as the blades separate somewhat, a folded lens 125 now held between the blades, with tongs 122d and 123d near the blade tips pushing into the lens sides. FIG. 19 shows super position of the arms in the wound or slit enabling arm movement back and forth in direction 140, corresponding to 40 in FIGS. 6 and 7, as well as arm rotation in the wound. In the modification of FIG. 18a, like FIG. 18, the tongs 122d' and 123d' are near the blade roots, whereby the lens is released to rotate oppositely to lens rotation in FIG. 18, upon release. In FIG. 20, corresponding to FIG. 7, the arm 122f is now spread to the left of arm 123f, and the blades are increasingly separated to allow lens 125 pivoting and release.

In use, the folded lens is moved into the capsulorhexis and placed in the neutral position. The leading edge of the lens is placed beneath the anterior capsule. The haptics are readily rotated posteriorly into the bag. This assists in the implantation of the lens before separating the blades. With the blades separating, the lagging edge of the lens escapes first while the leading edge is held 30–60 seconds longer. This produces a very controlled non-explosive lens implant release. The lagging edge of the optic advantageously moves posteriorly into the bag, its haptic also expands slowly. The remaining portion of the lens that is still grasped and is held posterior to the anterior capsule in the neutral position. The haptics are readily rotated posteriorly into the bag all of which assists in the implantation of the lens before spreading the blades. The final release of the leading portion of the lens is gentle and is especially achievable with 75% of the lens compression already dissipated.

Because the shafts are superimposed, slightly off center, the advantageous illusion of a single, narrow shaft persists, whereby the user is not confused. See FIG. 13. This is of further advantage when the transitional area of the distal shaft is bent abruptly in an area not over 2 mm long. The overall length of the forceps lies only in the anterior chamber and can be reduced to (6+2)=8 mm. In this manner the spreading transitional area of the shaft and blade will not occupy any space in the corneal scleral or limbal wound. If the shafts are long enough so as to not only extend out of the corneal scleral wound, and also long enough to extend out of the wound of the scleral tunnel, then one folding forceps will satisfy the needs for both short and lengthy scleral wounds. The parallel shafts 22f and 23f will remain in the perimeters of the corneal scleral wound, using 6 mm long blades.

The present forceps is made to achieve a non-explosive and non-sudden release of a compressed, folded silica lens implant, after having passed through a narrow, corneoscleral tunnel wound or slit without limitation of the spreading of the blades or spreading of the transitional, distal shafts (see FIGS. 8 and 9). Sufficient lateral strength of the debulked shafts (see FIGS. 8 and 9) is achieved while they still appear aesthetically narrow, strong, maneuverable, and safe. Apexed, horizontal design of the shafts is provided as shown.

Additional advantages imparted to the lens grasping blades, and their release of a folded lens through a capsulorhexis and into the intracapsular lens bad, are enabled through provision of convergence or taper of the blades, and tong tips of the blades. This permits the blades to control lens escape earlier (sooner) and gradually and nonexplosively, with less spread of the blades and shaft. Thus, controlled manipulation through a smaller wound is afforded.

Also significant are the crossing shafts with their transitional, distal and proximal angled extents connected to the blades and to the handles, such angled extents (as at 22e and 23e, and 22i and 23i) permitted to cross over in almost parallel arrangement. Excursion is conveyed over a greater distance; and thus the same instrument can be used for a limbal wound as well as in a wound 4 to 5 mm posterior to the limbus, in a very narrow tunnel 2.2 to 2.3 mm wide.

The instrument penetrates through long and short, narrow corneo-sclera wounds. The transitional, distal shafts and the blades do not impinge on the corneo-scleral wound, which would limit the lateral excursions of the blades. The lens grasping mechanism permits earlier and non-explosive release of the compressed silicon lens implant. The aesthetic appearance of the instrument enhances maneuverability of the forceps, in a smaller wound. Instrument arms provide strength with broad, horizontal, apexed (wedge shaped cross-section arms) lateral sides sliding past one another on separation of the blades. It enhances safety over conventional, non-vertical shafts, which let fluid escape from the eye with a danger of collapse of the anterior chamber on the instrument or during release of the lens implant.

In regard to lens nucleus cracking, and referring now to FIGS. 22–31, by creating a linear trough or crack 199 across the surface of the nucleus 200 one can pass or insert the oppositely and outwardly turned jaw edges 201a and 202a of jaws or blades 201 and 202 of the forceps instrument into the groove 199 and then cause the jaw edges to engage the walls 203 and 204 of the trough and force them to separate (by handle controlled jaw spreading) until the brittle hard floor 205 of the trough cracks and permits complete separation of the nuclear lens into halves. Four such lens portions may be cracked apart, by first grooving the lens as seen at 199 and 199a (two perpendicular intersecting grooves), in FIGS. 27 and 28. Arrow 197 shows 90° rotation of the nucleus 200 so that groove 199a' can be spread for cracking of its floor, after groove 199 is spread for cracking of its floor. These smaller lens sections 200 can be normally aspirated with the ability of elevating them out of danger, and then grooved as in phoco-emulsification, and fragmented into halves or quarters, as described.

Once again, separation of the cracking jaws, is achieved with the cross-action forceps as disclosed. See FIG. 22. The elongated shafts 222f and 223f will occupy the 3 mm corneo-scleral wound i.e. slit which will permit a 6 to 7 mm separation of the jaws or blades 201 and 202, which when inside the eye anterior chamber and lodged, graspingly in the trough 199, will separate the nucleus lens halves as described.

Note the jaws are designed, when completely closed, to pass down into the generally spherical or curved cross section groove (see FIG. 29), without out-turned edges 201a and 202a captured by the sides of the groove or trough. See also FIGS. 22 and 23 wherein the instrument elements are numbered to correspond to the same elements as seen in FIGS. 6 and 7, above, the numbers in FIGS. 22 and 23 bearing an added prefacing numeral 2.

Figure 24:
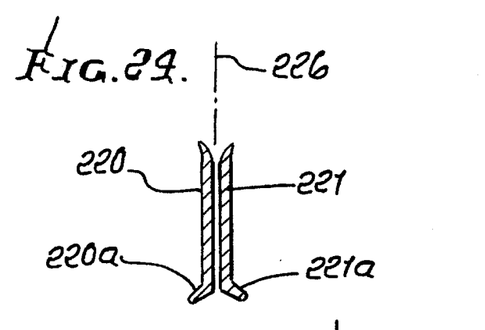
FIGS. 24, 25 and 26 are cross sections of various blade pairs.
Figure 25:
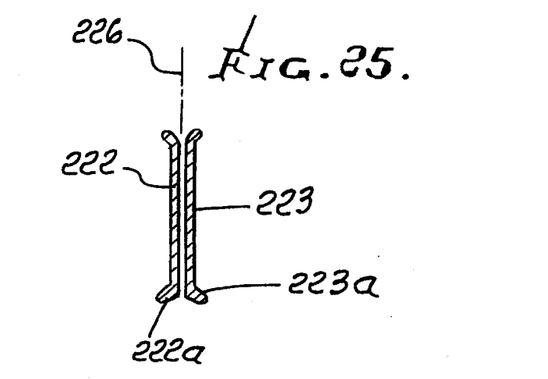
Figure 26:
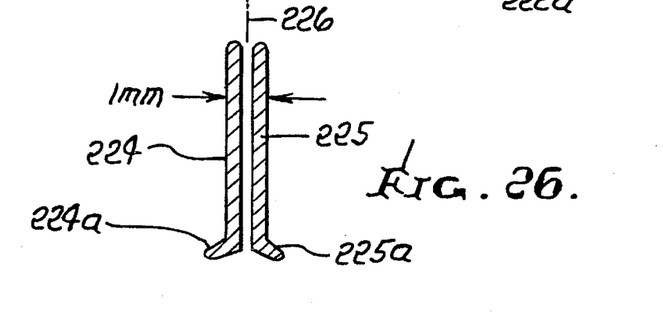

FIGS. 24–26 show different cross sections through blades with out-turned edges. See blades 220 and 221 with edges 220a and 221a; blades 222 and 223 with out-turned edges 222a and 223a; and blades 224 and 225, with out-turned edges 224a and 225a. Note indicated dimensions, with combined blade thickness less than 1 mm, and their representative dimensions, as drawn.

Figures 21, 22:
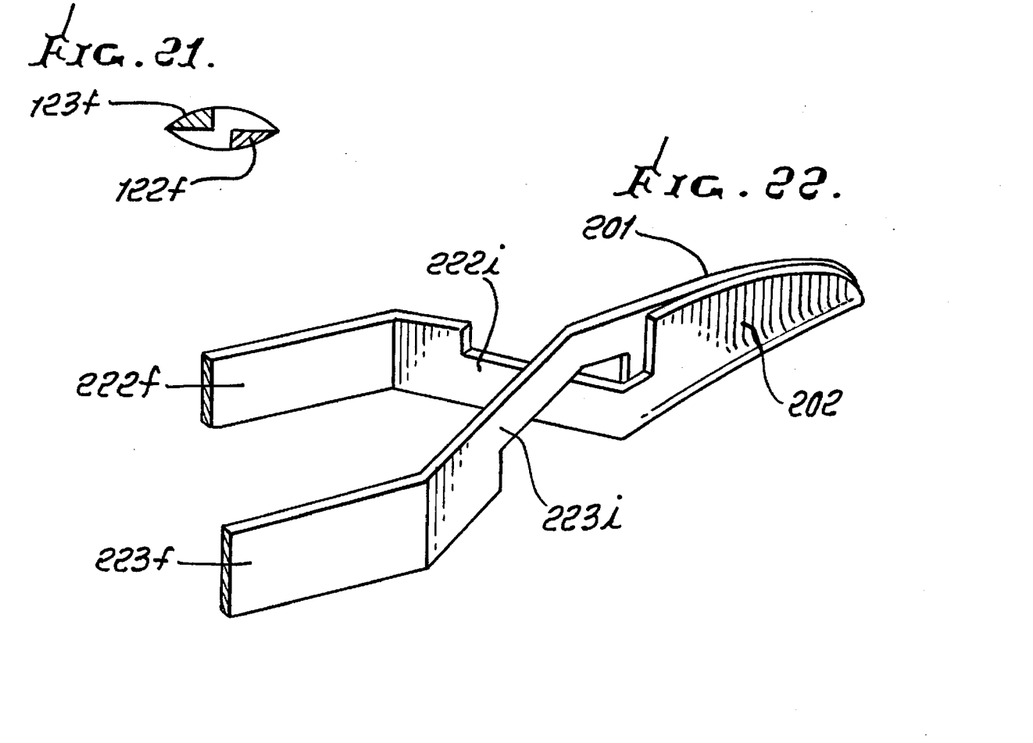
FIG. 22 is a perspective view of an instrument like that of FIGS. 6 and 7, but having blades configured for lens nucleus "cracking" or fragmenting.
Figure 23:
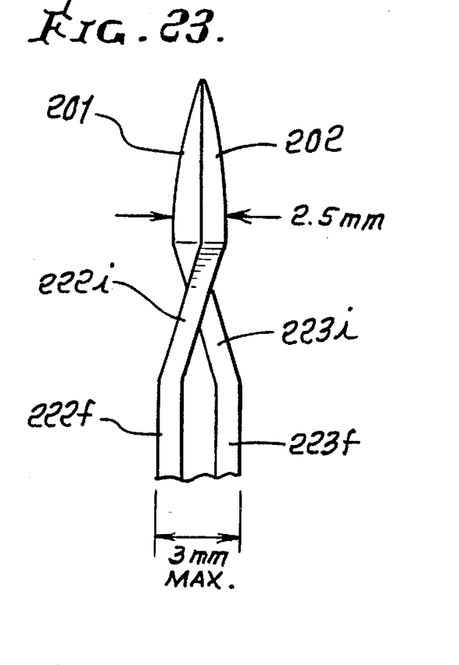
FIG. 23 is a top plan view of the FIG. 22 instrument, with blades closed together.

In regard to the FIG. 22 forceps, it comprises a) first and second arms, the first arm having a first handle and a first lens engagement blade spaced from the first handle, the second arm having a second handle and a second lens engagement blade spaced from the second handle, the blades 201 and 202 extending generally longitudinally in laterally spaced relation and at opposite side of a bisecting plane 226, b) the first arm having a primary section and a secondary section, the secondary arm section extending between the first handle and first blade, the second arm having a primary section and a secondary section, the secondary arm section extending between the second handle and second blade, the blades being movable by the handles and arm sections between closed and open positions relative to the lens or lens nucleus, the arm primary sections 222i and 223i extending in cross-over relation to define a cross-over locus, when the blades are in closed position, as in FIG. 23, c) the secondary arm sections 222f and 223f extending generally longitudinally in substantially parallel relation at opposite sides of plane 226, and with spacing therebetween less than about 4 mm.

Figure 23A:
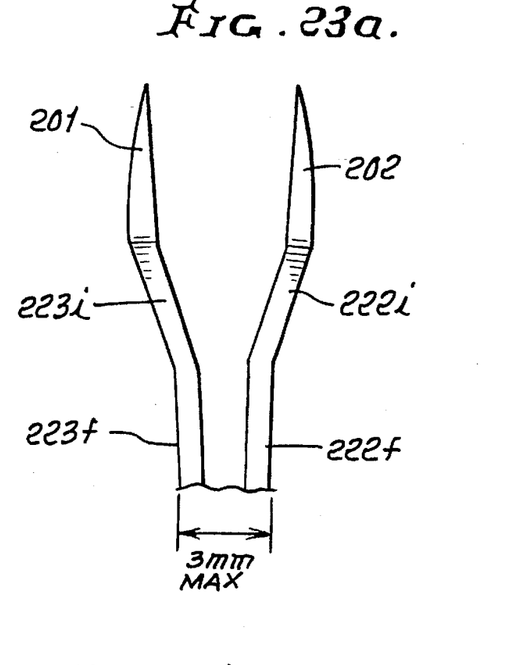
FIG. 23a shows the blades spread apart as during lens nucleus cracking.

FIG. 23 shows blades 201 and 202 closed together as during entry into the eye; and FIG. 23a shows the blades separated as during spreading and cracking of the lens nucleus.

Figure 27:
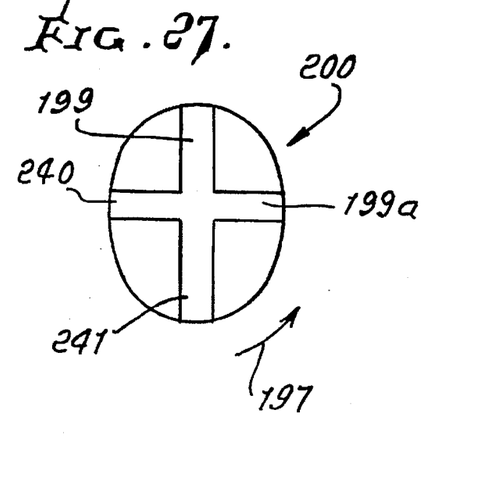
FIG. 27 is a view of a grooved lens hardened nucleus, to be "cracked"
Figure 28:
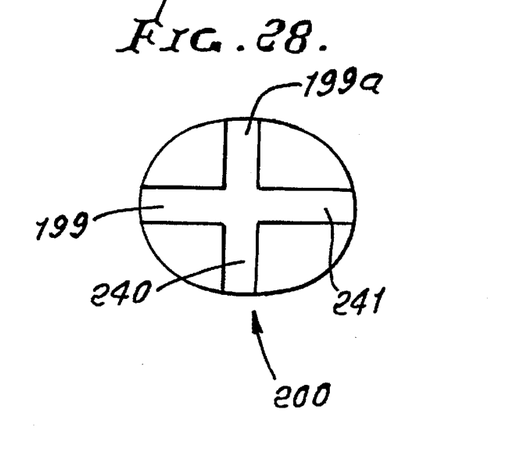
FIG. 28 is a view like FIG. 27, but showing cracking.
Figure 29:
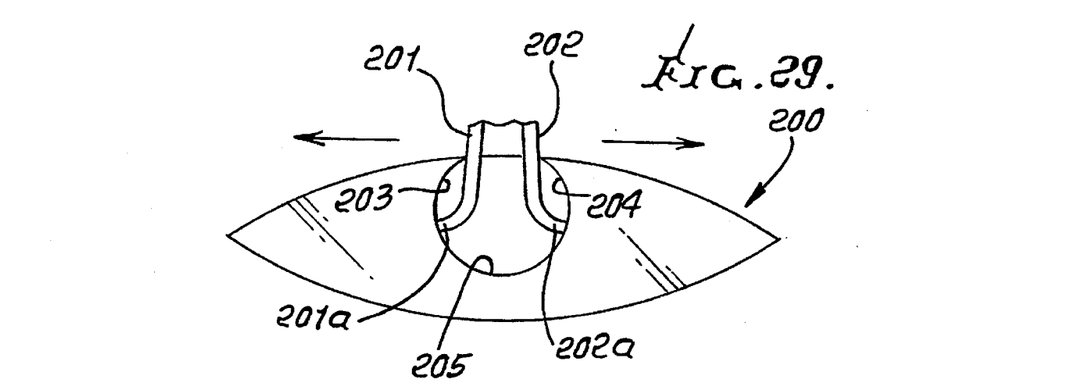
FIG. 29 is an enlarged section taken through a lens hardened nucleus, showing blade edge insertion into a groove formed in the nucleus.
Figure 30:
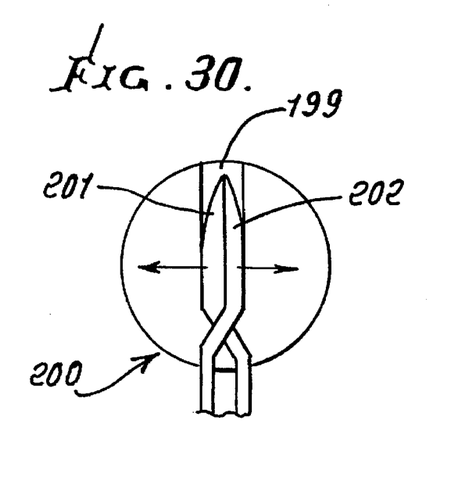
FIGS. 30 and 31 show a two-step cracking procedure.
Figure 31:
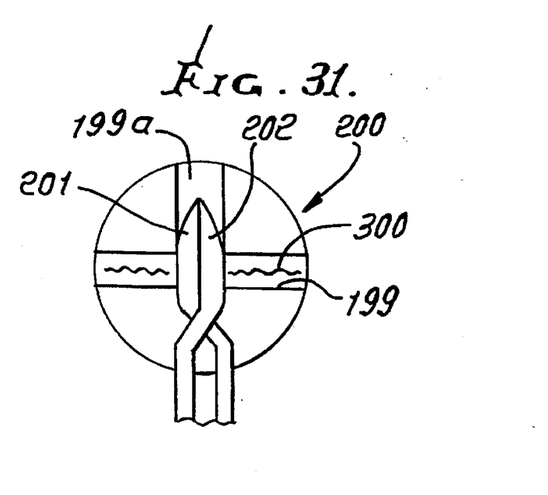

FIGS. 27 and 28 show grooves 199 and 199a and 240 and 241 formed at right angles to one another in the surfaces of a hardened lens nucleus, as by use of a phoco cutter, as is known. FIG. 30 shows the blades 201 and 202 inserted into a groove 199 for spreading and cracking the nucleus under that groove. The nucleus 200 is then rotated 90° and the blades inserted into groove 199a, as in FIG. 31. Note crack 300 formed in groove 199. The blades are again separated to again crack the nucleus under groove 199a., i.e. a two-step process. The nucleus is thereby cracked or fragmented into four wedge-shaped quadrants, easily retrieved from the eye, as by use the instrument described in my U.S. Pat. No. 4,957,505.

It can be very rewarding to be able to dilate a very small miotic pupil during a cataract extraction, such dilation also lessening risk of problems during cataract removal surgery.

Sufficient enlargement of the pupil permits a normal surgical removal of the anterior lens capsule (capsulorhexis), fragmentation and aspiration of the remaining cataractous opacities, polishing the central posterior lens capsule and proper visualization for the intraocular implantation of the lens.

Features of the present instrument that permit such dilation of the pupil, up to 7 mm, while the instrument occupies a 3 mm corneo-scleral wound, include the prolonged smallness of the points of arm section crossing.

The modified instrument as shown in FIGS. 22–26 also enables its jaws to function at variable distances from the incision wound while such jaws reside in the anterior chamber (from 3 to 10 mm). The continuous cross-over remains in the 3 mm incision wound or slit while jaw separation (for dilating) occurs.

In the past, a surgical sphincterotomy followed by a peripheral iridectomy and then a plastic repair of the iris defect, if possible, was attempted.

The surgical ease, and time saved, with less cost and less post-operative reaction, as well as less recuperative time to achieve clear vision is readily available to the eye surgeon through use of the present dilation forceps.

Pupil dilation lets one see precisely into the depths of the lens capsule "bag" which thereby permits a permanent and accurately placed intra capsular lens implant.

Without pressure on the handles of the instrument the jaws are closed together; yet as soon as the pupil's edges are engaged with the notched lateral sides of the jaws, such edges can be easily captured and forcibly enlarged laterally to a diameter of 6–7 mm. Such enlargement affords a sufficient aperture to enable the surgeon to see all the details of the capsulorhexis, as previously described.

Figure 32:
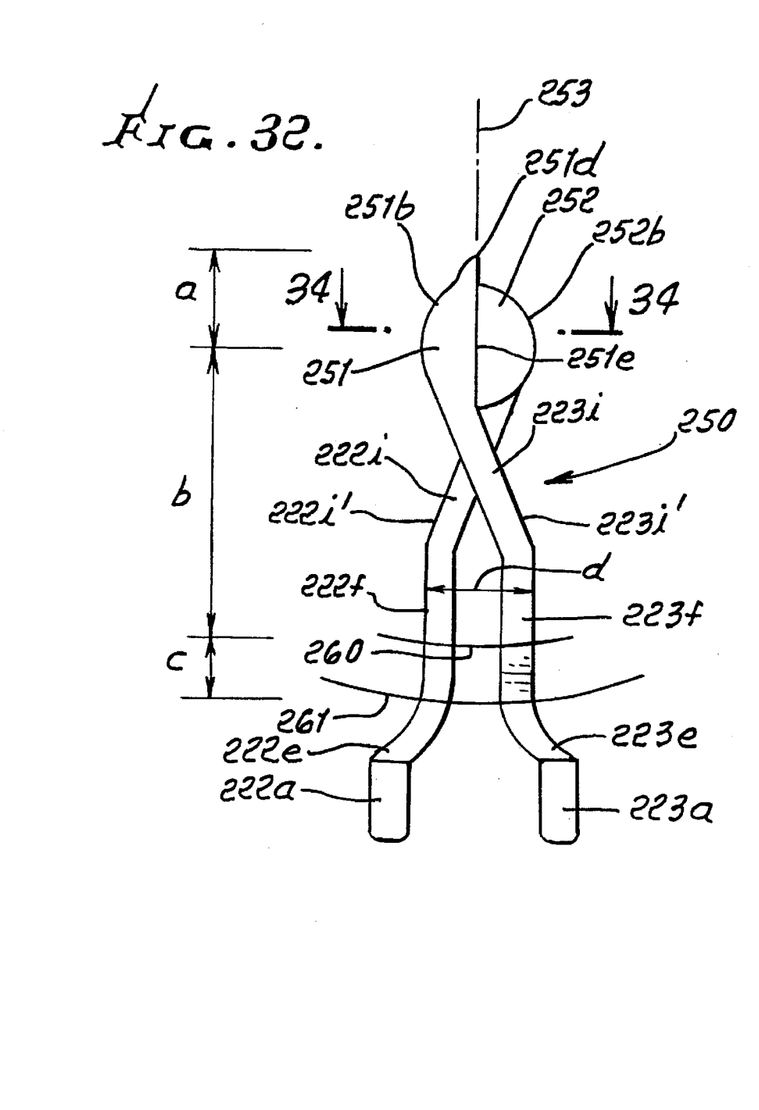
FIG. 32 is a plan view like FIG. 23, but showing arcuate blade notches suitable for pupil dilation.
Figure 32A:
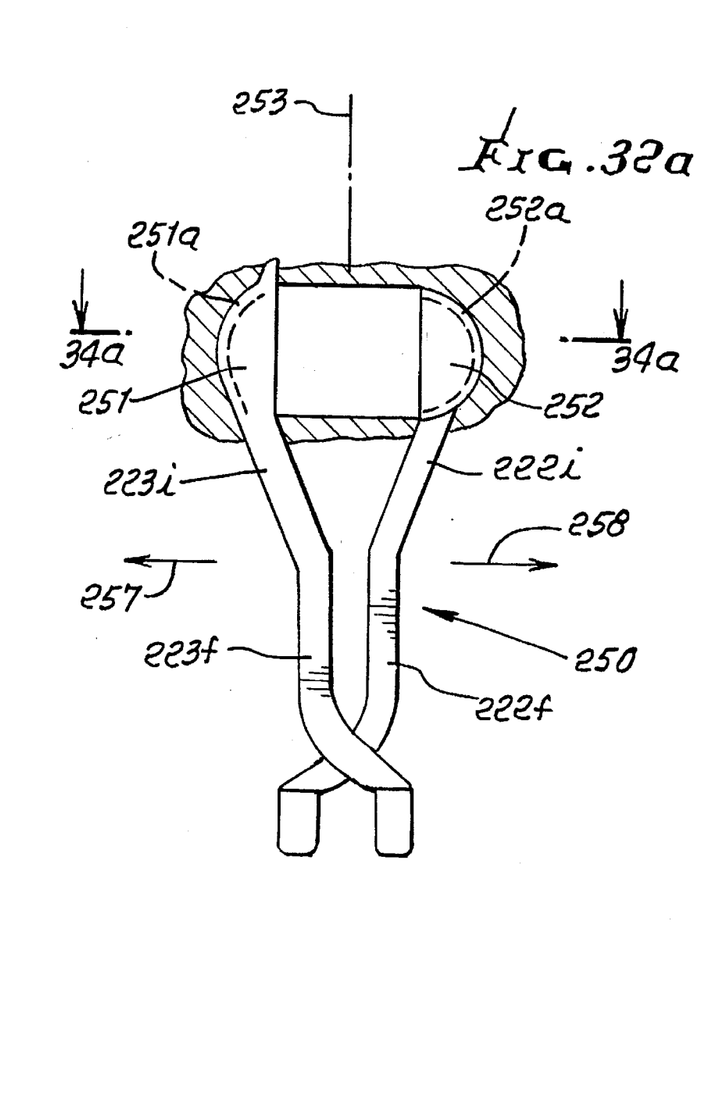
FIG. 32a shows blade separation and pupil dilation via notch gripping of pupil edges.
Figures 33, 34, 34A, 35, 36:
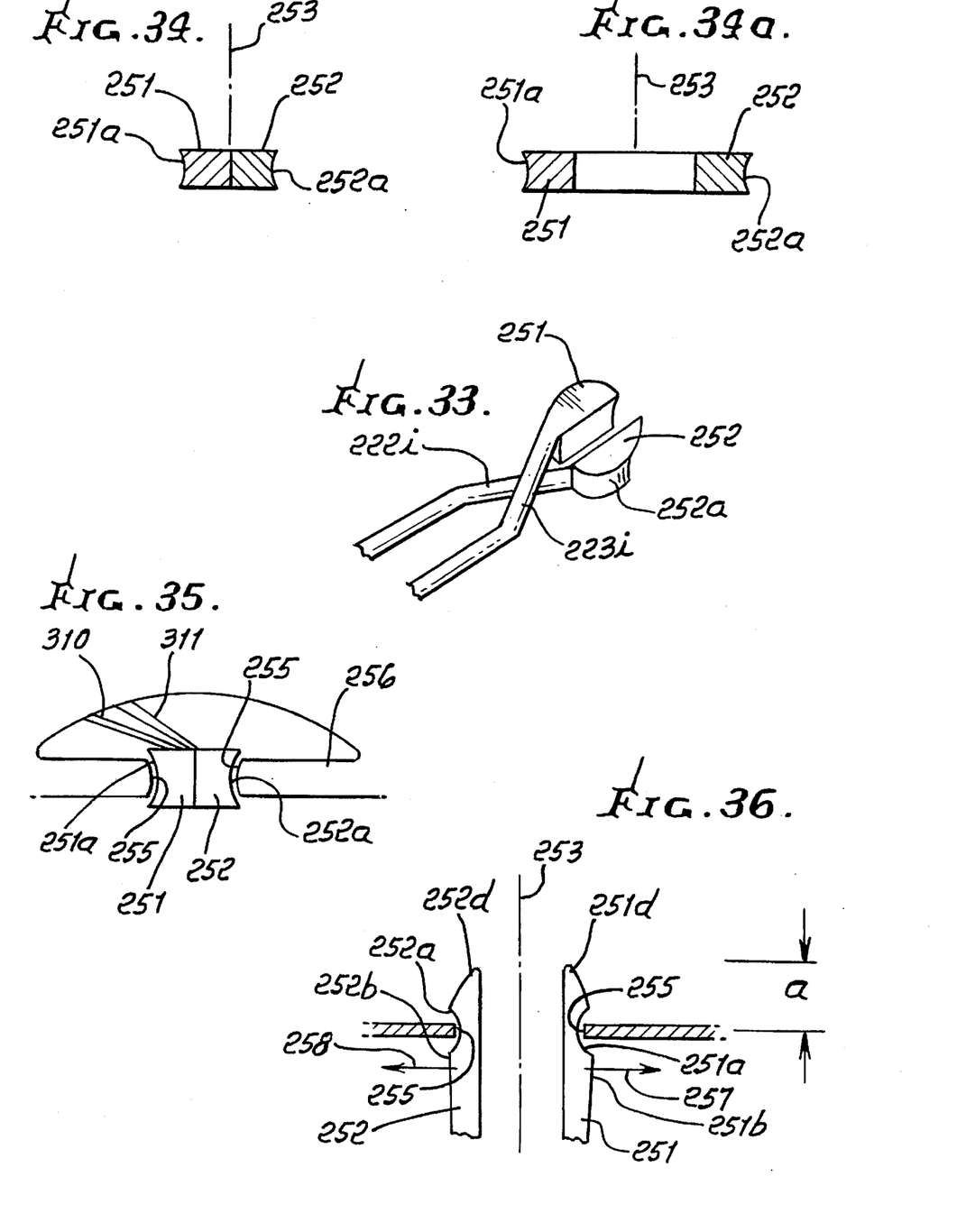

In this regard, the instrument 250 of FIGS. 32–34 and FIGS. 32a and 34a is generally like FIGS. 22 and 23, excepting that the blades 251 and 252 have arcuate notches 251a and 252a formed in the blade sides 251b and 252b facing away from bisecting mid-plane 253. See also FIG. 36. FIG. 35 shows the blades penetrating deeply into the eye, with notches 251a and 252a positioned to grip the arcuate edge or edges 255 of the eye pupil 256, and lines 310 and 311 show eye entry paths. FIGS. 32a and 34a are views showing such gripping, and dilation, as the blades are moved apart (as indicated by arrows 257 and 258) from bisecting plane 253. Note in FIGS. 32 and 32a the merging of the outer side 222i' of arm primary section 222i with arcuate notch 252a; and the merging of the outer side 223i' of arm primary section 223i with arcuate notch 251a. Note in FIG. 32a that arms 222f and 223f have crossed over one another during blade spreading. Notches 251a and 252a are convex away from plane 253, in the plane of FIG. 32; and those notches are concave toward plane 253, in the plane of FIG. 34.

Relative representative dimensions are as follows, as seen in FIG. 32:

"a"—distance from blade pointed end 251d to center 251e of elements 251 and 252 (center of eye);

"b"—distance from center 251e to locations 260 at the limbus, i.e. on the instrument elongated arms 222f and 223f;

"c"—distance from locations 260 to locations 261 where arm sections 222e and 223e enter the eye;

"d"—overall width of arms and spacing therebetween when the blades are closed together (overall width of blades 251 and 252 is about the same as "d")

where

"a" is about 2½ mm

"b" is about 6–8 mm

"c" is about 2–4 mm

"d" is about 3 mm.

I claim:

1. An improved intraocular lens forceps and lens combination, comprising
   a) first and second arms, the first arm having a first handle and a first eye element engagement blade spaced from the first handle, the second arm having a second handle and a second eye element engagement blade spaced from the second handle, the blades extending generally longitudinally in laterally spaced relation and at opposite sides of a bisecting plane,
   b) the first arm having a primary section and a secondary section, the primary and secondary arm sections extending between the first handle and first blade, the second arm having a primary section and a secondary section, the primary and secondary arm sections of the second arm extending between the second handle and second blade, the blades being movable by the handles and arm sections between closed and open positions relative to the lens, the arm primary sections extending in cross-over relation to define a cross-over locus, when the blades are in said closed position, the arms having an additional cross-over locus when the blades are in said open position,
   c) the arm secondary sections extending generally longitudinally in substantially parallel and elongated relation, and with spacing therebetween less than about 4 mm,
   d) there being a folded, plastic lens gripped by the blades in said closed position thereof.

2. The forceps of claim 1 wherein when said blades are increasingly separated from one another, said spacing between said secondary arm sections is decreased.

3. The forceps of claim 1 wherein said blades have jaw edges to engage and separate opposite sides of a groove in an eye lens hardened nucleus when the blades are increasingly separated, thereby to fracture said hardened nucleus.

4. The forceps of claim 1 wherein said blades, when in said closed position have a combined thickness of less than about 1 mm.

5. The forceps of claim 1 wherein said arm secondary sections are positioned such that when the blades are in said closed positions one arm secondary section extends at one side of said plane and the other arm secondary section extends at the other side of said plane, and when the blades are in said open positions said one arm secondary section extends at said other side of said plane and said other arm secondary section extends at said one side of said plane.

6. The forceps of claim 1 wherein the arm secondary sections have a maximum lateral separation, and longitudinal lengths greater than their said maximum lateral separation, to allow movement back and forth in an incision wound in the eye corneo-scleral limbus via which the blades are inserted into the eye.

7. The forceps of claim 1 wherein said first blade remains at said one side of said plane as the blades are moved between said closed and open positions, and the second blade remains at said other side of said plane as the blades are moved between said closed and open positions.

8. The forceps of claim 7 wherein said first handle remains at said other side of said plane as the blades are moved between said closed and open positions, and the second handle remains at said one side of said plane as the blades are moved between said closed and open positions.

9. The forceps of claim 1 wherein said arm secondary sections have lateral separation in each of closed and open positions of the blades, said lateral separations being equal.

10. The forceps of claim 1 wherein the arm primary sections extend at opposite angles relative to said plane.

11. The forceps of claim 1 wherein the arm primary sections have lengths substantially less than the longitudinal lengths of said arm secondary sections.

12. The forceps of claim 1 wherein said lens has folded sections, and haptics respectively connected to said sections and extending in a relatively folded state.

13. The forceps of claim 1 including pupil edge gripping means on the blades to dilate the pupil when the blades are moved to open positions, said means facing relatively away from one another.

14. An improved intraocular lens forceps, comprising
   a) first and second arms, the first arm having a first handle and a first eye element engagement blade spaced from the first handle, the second arm having a second handle and a second eye element engagement blade spaced from the second handle, the blades extending generally longitudinally in laterally spaced relation and at opposite sides of a bisecting plane,
   b) the first arm having a primary section and a secondary section, the primary and secondary arm sections extending between the first handle and first blade, the second arm having a primary section and a secondary section, the primary and secondary arm sections of the second arm extending between the second handle and second blade, the blades being movable by the handles and arm sections between closed and open positions relative to the lens, the arm primary sections extending in cross-over relation to define a cross-over locus, when the blades are in said closed position, the arms having an additional cross-over locus when the blades are in said open position,
   c) the arm secondary sections extending generally longitudinally in substantially parallel and elongated relation, and with spacing therebetween less than about 4 mm,
   d) said blades having jaw edges to engage and separate opposite sides of a groove in an eye lens hardened nucleus when the blades are increasingly separated, thereby to fracture said hardened nucleus,
   e) and wherein said jaw edges diverge relatively away from one another, in the direction of said plane.

15. The forceps of claim 14 wherein the arm primary sections are laterally separated when the blades are in closed position.

16. An improved intraocular lens forceps, comprising
   a) first and second arms, the first arm having a first handle and a first eye element engagement blade spaced from the first handle, the second arm having a second handle and a second eye element engagement blade spaced from the second handle, the blades extending generally longitudinally in laterally spaced relation and at opposite sides of a bisecting plane,
   b) the first arm having a primary section and a secondary section, the primary and secondary arm sections extending between the first handle and first blade, the second arm having a primary section and a secondary section, the primary and secondary arm sections of the second arm extending between the second handle and second blade, the blades being movable by the handles and arm sections between closed and open positions relative to the lens, the arm primary sections extending in cross-over relation to define a cross-over locus, when the blades are in said closed position, the arms having an additional cross-over locus when the blades are in said open position, c) the arm secondary sections extending generally longitudinally in substantially parallel and elongated relation, and with spacing therebetween less than about 4 mm, d) and wherein said blades have notches therein openly facing away from said plane, for gripping and separating edges of an eye pupil when the blades are moved apart.

17. An improved intraocular lens forceps, comprising a) first and second arms, the first arm having a first handle and a first eye element engagement blade spaced from the first handle, the second arm having a second handle and a second eye element engagement blade spaced from the second handle, the blades extending generally longitudinally in laterally spaced relation and at opposite sides of a bisecting plane, b) the first arm having a primary section and a secondary section, the primary and secondary arm sections extending between the first handle and first blade, the second arm having a primary section and a secondary section, the primary and secondary arm sections of the second arm extending between the second handle and second blade, the blades being movable by the handles and arm sections between closed and open positions relative to the lens, the arm primary sections extending in cross-over relation to define a cross-over locus, when the blades are in said closed position, the arms having an additional cross-over locus when the blades are in said open position, c) the arm secondary sections extending generally longitudinally in substantially parallel and elongated relation, and with spacing therebetween less than about 4 mm, d) and wherein said blades have lens gripping tongs projecting toward said plane, to grip opposite sections of a folded lens, the tongs defining pivots about which the folded lens may pivot during unfolding release of the lens as the blades are moved from closed to open positions.

18. The forceps of claim 17 wherein the blades have tips remote from said secondary arm sections, said tongs located at said tips.

19. The forceps of claim 17 in combination with a folded plastic lens gripped by said blades in said closed position thereof.

20. The forceps of claim 17 in combination with a folded plastic lens defining said opposite sections which are gripped by said blades in said closed position with said tongs pushed into said respective opposite sections of said lens.

21. The forceps of claim 17 wherein said blades taper toward said plane in directions away from said secondary arm sections.

22. The method of using forceps in an eye and via a slit in the eye wall, that includes the steps:

a) providing a forceps having first and second arms, the first arm having a first handle and a first eye element engagement blade spaced from the first handle, the second arm having a second handle and a second eye element engagement blade spaced from the second handle, the blades extending generally longitudinally in laterally spaced relation and at opposite sides of a bisecting plane, b) said first arm provided to have primary and secondary arm sections extending between the handle and the first blade, and said second arm provided to have primary and secondary arm sections extending between the second handle and second blade, the blades being movable by the handles and arm sections between closed and open positions, the arm primary sections defining a cross-over locus, when the blades are in closed position, the arms moved to define an additional cross-over locus when the blades are in open position, c) said arm secondary sections provided to extend generally longitudinally in substantially parallel and elongated relation at opposite sides of said plane and with spacing therebetween less than about 4 mm, d) providing a folded, plastic lens, e) manipulating said forceps thereby causing said blades to grip said folded plastic lens in said blade closed position; said lens into the eye.

23. The method of claim 22 including adjusting said forceps arm secondary sections lengthwise in said eye wall slit while maintaining said arm primary and secondary sections in predetermined spaced relation to said blades.

24. The method of claim 22 wherein the arms have additional sections between the blades and said arm primary and secondary sections, and including the step of maintaining said arm additional sections in cross-over relation when the blades are in said closed position.

25. An improved intraocular lens forceps, comprising a) first and second arms, the first arm having a first handle and a first eye element engagement blade spaced from the first handle, the second arm having a second handle and a second eye element engagement blade spaced from the second handle, the blades extending generally longitudinally in laterally spaced relation and at opposite sides of a bisecting plane, b) the first arm having a primary section and a secondary section, the primary and secondary arm sections extending between the first handle and first blade, the second arm having a primary section and a secondary section, the primary and secondary arm sections of the second arm extending between the second handle and second blade, the blades being movable by the handles and arm sections between closed and open positions relative to the lens, the arm primary sections extending in cross-over relation to define a cross-over locus, when the blades are in said closed position, the arms having an additional cross-over locus when the blades are in said open position, c) the arm secondary sections extending generally longitudinally in substantially parallel and elongated relation, and with spacing therebetween less than about 4 mm, d) and including lens nucleus gripping protrusions on the blades to grip walls of a groove in the lens nucleus when the blades are separated, said protrusions projecting relatively away from one another.

26. The forceps of claim 25 wherein said arm secondary sections are longitudinally elongated and positioned to slide past one another laterally, during blade movement to open positions.

* * * * *